United States Patent [19]

Winter, III

[11] 4,079,093
[45] Mar. 14, 1978

[54] AROMATIC HYDROCARBON ALKYLATION PROCESS

[75] Inventor: George R. Winter, III, Mt. Prospect, Ill.

[73] Assignee: UOP Inc., Des Plaines, Ill.

[21] Appl. No.: 801,984

[22] Filed: May 31, 1977

[51] Int. Cl.² .............................. C07C 3/52; C07C 3/62
[52] U.S. Cl. .............................. 260/671 R; 260/672 T; 260/674 R
[58] Field of Search ............ 260/671 R, 672 T, 674 R

[56] References Cited

U.S. PATENT DOCUMENTS

| | | | |
|---|---|---|---|
| 2,971,992 | 2/1961 | Bloch | 260/671 R |
| 3,054,727 | 9/1962 | von Kessel et al. | 260/674 R |
| 3,126,421 | 3/1964 | Jones | 260/671 R |
| 3,200,163 | 8/1965 | Fenske | 260/671 R |
| 3,631,122 | 12/1971 | Berger | 260/671 R |
| 3,894,090 | 7/1975 | Cleveland | 260/671 R |

*Primary Examiner*—Delbert E. Gantz
*Assistant Examiner*—C. E. Spresser
*Attorney, Agent, or Firm*—James R. Hoatson, Jr.; John F. Spears, Jr.; William H. Page, II

[57] ABSTRACT

A process for the alkylation of an aromatic hydrocarbon with an olefinic hydrocarbon wherein a gaseous catalyst promoter is circulated through the alkylation zone effluent separation equipment including a first fractionation column. Part of the motive force for this promoter circulation is derived from depressurizing the vaporous phase of the alkylation zone effluent through an ejector which draws a suction on the overhead receiver of the fractionation column.

8 Claims, 1 Drawing Figure

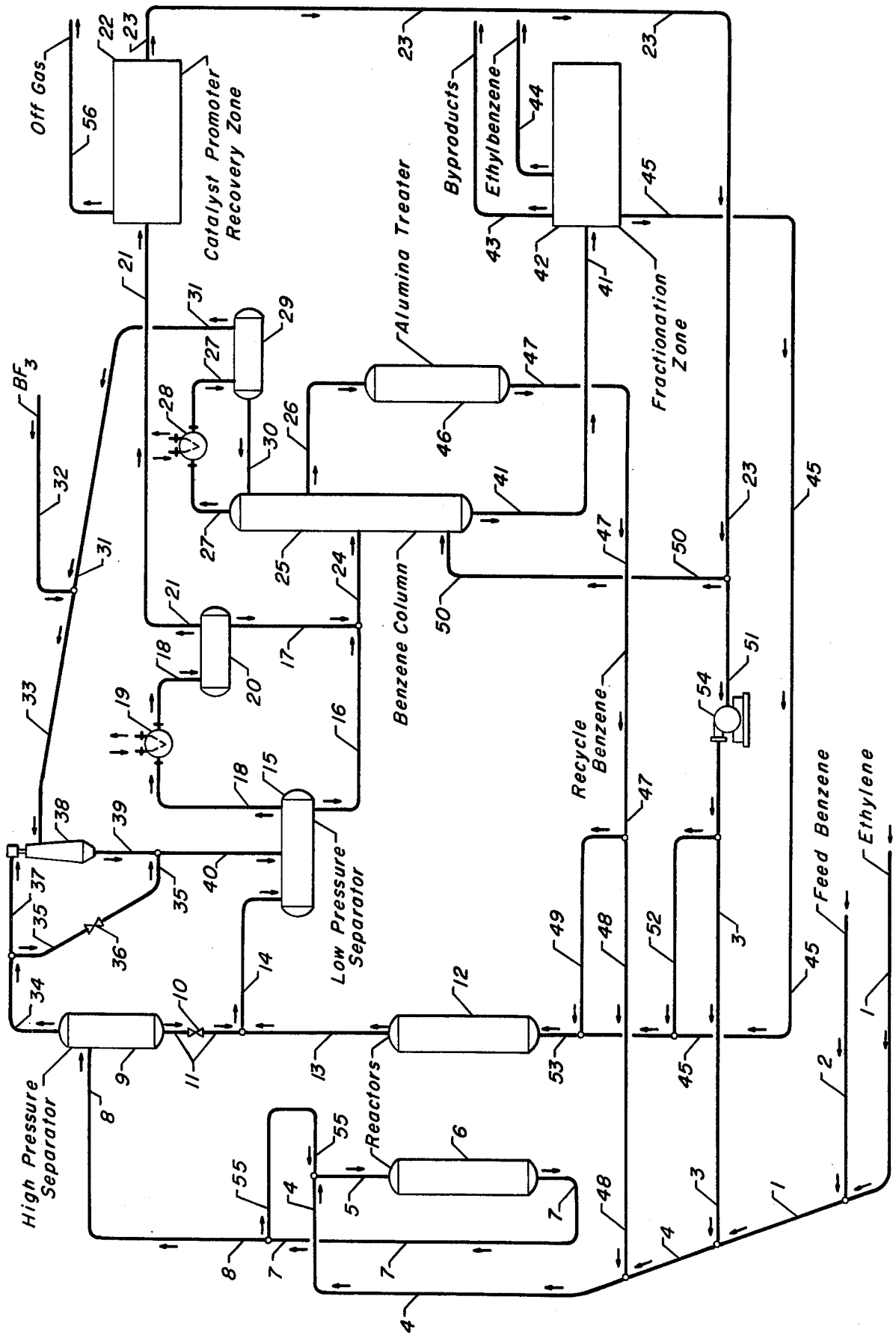

AROMATIC HYDROCARBON ALKYLATION PROCESS

FIELD OF THE INVENTION

The invention relates to a hydrocarbon conversion process. The process more specifically relates to a process for the alkylation of aromatic hydrocarbons by the introduction of an acyclic side chain. The invention also relates to the separation of the alkylation zone effluent produced in such a process. The invention therefore relates to processes similar in nature to those found in Class 260-671.

PRIOR ART

The alkylation of aromatic hydrocarbons is a well developed art, and processes for the alkylation of aromatic hydrocarbons are in widespread use. A wide range of catalysts are used in these processes. The preferred catalytic system for use in the subject process is described in U.S. Pat. Nos. 3,894,090 (Cl. 260-671); 3,631,122 and 2,971,992. The latter reference shows the passage of the alkylation zone effluent into a vapor-liquid separator, with a vapor stream comprising boron trifluoride, unreactive gases and the aromatic hydrocarbon being removed from the separator and passed into a countercurrent gas-liquid absorption zone. A stream of polyalkylated aromatic hydrocarbons is fed to the top of this zone to effect the recovery of the boron trifluoride and aromatic hydrocarbon. The unreactive gases are vented from the top of this zone.

The preferred catalyst system is also described in U.S. Pat. No. 3,126,421 (Cl. 260-671). In the alkylation process presented by this reference the effluents of an alkylation zone and a transalkylation zone are combined and passed into a flash drum. The liquid removed from the flash drum is passed into a benzene column. The vapor removed from the flash drum is cooled and passed into a vapor-liquid separator. The vapor removed from this separator is passed into the absorber of a boron trifluoride recovery zone comprising an absorber and a stripper. The enriched boron trifluoride produced in this zone is recirculated to the alkylation and transalkylation zones. This same reference also shows the removal of a boron trifluoride-containing overhead vapor from the benzene column. This overhead vapor stream is, however, recycled to the alkylation zone and not passed into a reaction zone vapor-liquid separator as in the present invention. Another feature illustrated by this reference is the production of a benzene recycle stream from the overhead vapors removed from the benzene column.

Previously cited U. S. Pat. No. 3,894,090 shows a benzene recycle stream withdrawn from the benzene column as a sidecut stream. This reference also describes the passage of boron trifluoride into the benzene column to prevent the precipitation of relatively non-volatile hydrate of boron oxide commonly referred to as borates.

SUMMARY OF THE INVENTION

The invention provides a process for the alkylation of aromatic hydrocarbons wherein part of the motive force required for the circulation of a fractionation column off-gas stream comprising a gaseous catalyst promoter, such as boron trifluoride, is provided by depressurizing the effluent of the alkylation zone through an ejector. This ejector is used to pump the overhead vapors of the fractionation column into a vapor-liquid separation zone to which the alkylation zone effluent is charged. The vapors separated in this zone are then passed into a catalyst promoter purification zone. The invention thereby provides an alkylation process requiring a smaller compressor and having lower operating costs than the prior art, which, for instance, compressed the overhead vapors of the fractionation column and passed them into the alkylation zone.

DESCRIPTION OF THE DRAWING

The Drawing illustrates the preferred embodiment of the invention. For clarity and simplicity various subsystems and apparatus associated with the operation of the process have not been shown. These items include flow and pressure control valves, pumps, temperature and pressure monitoring systems, reactor and fractionator internals, etc., which may be of customary design. This representation of the preferred embodiment is not intended to preclude from the scope of the invention those other embodiments set out herein or which are the result of reasonable and normal modification of these embodiments.

Referring now to the drawing, a feed stream comprising ethylene enters the process through line 1 and is admixed with a feed stream comprising benzene which enters through line 2. The resultant admixture is carried by line 1 to the junction with line 3, where it is commingled with a recycle vapor stream comprising boron trifluoride. The feed material continues through line 4 and is admixed with a portion of a recycle benzene stream carried by line 48. Line 4 carries the resultant mixture of benzene, ethylene and boron trifluoride to the junction with line 55 where it is combined with a recycled portion of the alkylation zone effluent, which has been cooled by a means not shown. This produces a combined alkylation zone feed stream which is passed into the alkylation reactor 6 through line 5. The effluent of the alkylation reactor is removed in line 7 and divided into the portion which is recycled through line 55 and a second portion which is passed through line 8 into a vapor-liquid separator 9.

The net effluent stream of the alkylation reactor is separated into a vapor stream comprising boron trifluoride and possibly other non-reactive gases, such as nitrogen and paraffins which were contained in the ethylene feed stream, and which is removed in line 34, and a liquid stream comprising benzene, the product ethylbenzene and polyalkylated benzenes. The liquid stream is removed in line 11 at a rate controlled by valve 10 which preferably is operated by a level control means sensing the liquid level in the separator 9. The liquid stream in line 11 is combined with the effluent stream of a transalkylation reactor 12 which is carried by line 13. The effluent stream of the transalkylation reactor comprises benzene, ethylbenzene, polyalkylated benzenes and boron trifluoride. Line 14 carries the resultant admixture of these two streams into a separating vessel 15. A liquid phase stream is removed from this separating vessel in line 16. A vapor stream comprising boron trifluoride is removed from the separating vessel 15 in line 18 and passed through a cooler 19. This results in the condensation of readily condensible hydrocarbons, such as benzene and ethylbenzene, which are collected as a liquid phase in a second separating vessel 20. The uncondensed vapors, including boron trifluoride are removed from the second vessel in line 21, and the condensate is removed in line 17. The condensate is then combined with the liquid stream from the first separating vessel and passed into line 24.

Material in line 24 is passed into a benzene column 25. Also passed into this column is a stream of vaporous boron trifluoride from line 50. The boron trifluoride and various relatively volatile hydrocarbons rise through the benzene column and are removed as an overhead vapor stream in line 27. The overhead vapor stream is passed through overhead condenser 28 which causes the condensation of benzene and other hydrocarbons having similar or higher boiling points. The overhead of the benzene column is then passed into an overhead receiver 29 and separated into a liquid phase reflux stream removed in line 30 and a vapor stream removed in line 31. This vapor stream comprises boron trifluoride and such relatively non-condensible light gases as nitrogen, methane or ethane which were contained in the ethylene feed stream. A stream of makeup boron trifluoride is passed into the process through line 32. The resultant boron trifluoride enriched vapor stream is caused to pass through line 33 by the suction generated in an ejector 38. This suction is created through the depressurization of the relatively high pressure vaporous portion of the alkylation zone effluent passing through line 34. At least a portion of the vaporous effluent is used as the motive stream passed into the ejector in line 37. A second portion of the vaporous effluent may be bypassed around the ejector through line 35 at a rate controlled by valve 36. The effluent of the ejector is admixed with any vaporous alkylation zone effluent which has been bypassed around the ejector and is then passed into the first settling vessel 15 through line 40. In this manner the relatively high pressure of the alkylation zone is utilized to remove the net uncondensed overhead vapors of the benzene column and to circulate these vapors into a first receiving vessel. From the first receiving vessel these vapors flow through line 18 and 21 in admixture with the vapors released from the liquid passing through line 14.

A vapor stream in line 21 is passed into a promoter recovery zone 22. Preferably, this zone comprises a countercurrent absorption column and a stripping column. The operation of this preferred recovery zone configuration is described in greater detail herein. An off-gas stream comprising such impurities as nitrogen, methane and ethane is removed from the process in line 56. A purified stream of boron trifluoride vapors is removed in line 23 for recycling within the process. A first portion of this purified stream is passed into the bottom of the benzene column through line 50. The remaining portion passes through line 51 and is pressurized in a compressor 54. This pressurized portion is then divided between the boron trifluoride stream passed to the alkylation zone through line 3 and the boron trifluoride stream passed to the transalkylation zone through line 52.

A sidecut stream comprising benzene is removed from the benzene column in line 26 and passed through alumina treater 46. This fractionation product stream is then recycled through line 47 to provide the recycle benzene which is passed into the alkylation zone via line 48 and into the transalkylation zone via line 49. A net bottoms stream is removed from the benzene column in line 41 and passed into a fractionation zone 42. Preferably, this fractionation zone comprises two fractionation columns as described in greater detail herein. A net overhead product stream of substantially pure ethylbenzene is removed from the first fractionation column and forms the product stream removed in line 44. Preferably, a second fractionation column separates from the remaining hydrocarbons a relatively small by-product stream removed in line 43 and which comprises various high boiling aromatic hydrocarbons and polymers. This leaves the intermediate hydrocarbons including various bi- and tri-alkylated ethylbenzenes which are concentrated into a recycle stream removed in line 45. This recycle stream is combined with the boron trifluoride from line 52 and a recycle benzene stream from line 49 and passed into the transalkylation reactor through line 53.

DETAILED DESCRIPTION

The alkylation of aromatic hydrocarbons finds utility in several industrial processes. It is performed for instance to effect the production of ethylbenzene from benzene and ethylene, with much of the product ethylbenzene being subsequently dehydrogenated to produce styrene. In a similar manner, isopropylbenzene or cumene may be formed by the reaction of propylene and benzene. Cumene is used in the synthesis of phenol, acetone, alphamethylstyrene and acetophenone. These cumene-derived chemicals are intermediates in the production of resins for plastics including nylon. Other aromatic hydrocarbons are possible feedstocks for use in the subject invention. These include alkyl-substituted aromatics such as toluene, phenols and polycyclic aromatics. However, as the preferred embodiment of the invention concerns the alkylation of benzene and the prior art examples are often also based on the use of this feedstock, the invention will be described mainly in terms of benzene alkylation. This is not intended to in any way exclude other aromatic feedstocks from use in the invention.

Furthermore, the invention is one of general application within the broad field of hydrocarbon conversion processes. It may be applied to other specific reactions including reforming, dehydrogenation, isomerization of paraffins and aromatics, hydrodecyclization, hydroformylation, hydrodesulfurization, coal gasification and liquefaction, hydrocracking, esterification, methanation, hydrogenation and the alkylation of paraffinic or olefinic hydrocarbons. Any of these reactions could be performed in the reaction zone. In a similar manner the catalyst promoter recovery zone could be replaced by other types of purification operations, including gas concentration units. The basic concept is therefore a hydrocarbon conversion process in which a relatively high pressure mixedphase reaction zone effluent stream is separated into liquid and vapor phases, the vapor phase is depressurized through an ejector to thereby increase the pressure of a low pressure vapor stream and to pump the low pressure stream, or a portion thereof, into an intermediate pressure zone in admixture with at last some of the reaction zone effluent vapor.

The preferred catalyst system for use in the alkylation zone, and in the transalkylation zone if one is present, is one which utilizes a catalyst promoter which is vaporous at standard conditions of temperature and pressure. This catalyst promoter is preferably a halogen-containing compound chosen from the group consisting of boron trifluoride, boron trichloride, boron tribromide, hydrogen chloride, carbon tetrachloride, hydrogen fluoride, hydrogen bromide, ammonium fluoride, ammonium chloride, ammonium bromide and ammonium iodide. More preferably the catalyst promoter is a boron halide, with boron trifluoride being especially preferred.

The preferred catalyst system is described in U.S. Pat. Nos. 3,126,421 (Cl. 260-671); 3,631,122 and 3,894,090. The reaction zones contain a boron halide-promoted catalyst utilizing a solid carrier and maintained in an anhydrous condition. Preferably the boron halide is boron trifluoride and the carrier is an inorganic oxide. The carrier may be selected from among many inorganic oxides including alumina, silica, boria, oxides of phosphorus, titanium dioxide, zirconium dioxide, chromia, etc., and various naturally occurring inorganic oxides of various states of purity, such as clay or diatomaceous earth. Of the above-mentioned inorganic oxides, the gamma and theta forms of alumina are most readily modified by boron trifluoride, and the use of one or both of these materials is preferred. The reaction zones may also or alternatively contain a bed of a crystalline aluminosilicate zeolite.

Modification of the carrier may be carried out prior to or simultaneously with the initial passage of the reactants over the carrier. This modification is accomplished by the passage of a boron trifluoride-containing gas stream over a bed of the carrier material maintained at an elevated temperature of from about 300° to about 500° F. To maintain the catalyst in an active state during operation, boron trifluoride is recirculated to each reaction zone at the relatively small rates of about 2000 ppm. in the alkylation zone and about 3500 ppm. in the transalkylation zone. These two zones will be described more fully hereinafter. Generally, boron trifluoride is utilized as a pure vaporous material by the direct passage to the reaction zones while dissolved in the aromatic feed stream. Although an organic solvent solution of $BF_3$ may be employed, such a technique is not preferred since $BF_3$ complexes with a multitude of organic compounds, and the latter can react with either the aromatic or olefinic feed material. Required quantities of $BF_3$ are relatively small, and may be conveniently expressed as grams of $BF_3$ per mole of olefin. The quantity of $BF_3$ used may be less than 1.0 gram per gram mole of olefin and preferably is from about 0.1 to 1.0 gram per gram mole.

The preferred boron halide-promoted alkylation process utilizes two reaction zones to produce mono-alkylated aromatic hydrocarbons. The first reaction zone is used to alkylate the aromatic hydrocarbon, which in the preferred embodiment results in the formation of ethylbenzene. The second reaction zone is used to transalkylate polyalkylated aromatics produced in the first reaction zone. According to the prior art methods of operating this process, the liquid phase portion of the effluent streams of the two reaction zones are combined and fed into a single fractional distillation column, referred to as the recycle benzene column. The alkylation reaction zone is normally operated in a downflow manner at a temperature of from 100° to 600° F., with the preferred operating temperature being from 250° to 450° F. The transalkylation reaction zone is normally operated in an upflow manner and maintained at a higher temperature of from 350° F. to 450° F., but may vary in temperature from about 200° F. to 700° F. The pressure in either reaction zone may range from about atmospheric to 1500 psig., although it is presently desirable to use a pressure range of from about 300 psig. to 600 psig. The pressure is preferably chosen to be sufficient to maintain the aromatic hydrocarbon compounds in a liquid state.

To obtain a high selectivity for the production of a mono-alkylated benzene in the alkylation zone, it is best to have present from about 1.5 to about 5 moles of benzene for each mole of ethylene. This is also true for the alkylation of other aromatic hydrocarbons and other olefins. The olefins are therefore to be completely reacted in the alkylation reaction zone and are not present in the effluent of this zone. The excess aromatic hydrocarbon also tends to reduce the polymerization of the olefin and acts as a heat sink. To maintain the high excess of aromatic material, it is common practice to recirculate a large amount of unfractionated reactor effluent, which may be up to about 15 times as large as the reactor feed stream or net reactor product. The liquid hourly space velocity used in the alkylation reaction zone may vary between 0.5 and about 10.0.

In the transalkylation zone, an excess of unalkylated aromatic hydrocarbons over polyalkylated aromatic hydrocarbons is maintained, with the relative ratio being from about 1.5 to about 3 moles of unalkylated aromatic hydrocarbon per mole of polyalkylated aromatic hydrocarbon. The liquid hourly space velocity of the reactants in the transalkylation reaction zone is preferably between about 0.2 to about 3. In order to obtain essentially complete conversion of polyethylbenzenes, the charge rate to the transalkylation reaction zone is generally more than three times that of the polyethylbenzene make. This is because the transalkylation reactions of polyethylbenzenes proceed at a much slower rate than the initial alkylation reaction of benzene. This greater charge rate may be obtained by the recycling of a portion of the transalkylation zone effluent stream. Operating conditions in either reaction zone may be varied to correspond to the type of alkylation step which is effected therein and to provide optimum yields. Further details on the preferred alkylation process may be obtained by reference to U.S. Pat. Nos. 2,887,520 and 3,631,122.

The preferred catalyst system is troubled by the formation of boron oxide hydrates in the alkylation zone by the reaction of small amounts of water contained in the feed stream with the boron trifluoride. If left untreated, these non-volatile compounds settle on the internal surfaces of the downstream benzene column and its associated reboiler. This decreases the efficiency of the column and would eventually require the operation of the process to be terminated to allow removal of these deposits. A preferred method of preventing the deposition of the boron oxide hydrates, commonly referred to as borates, in the benzene column is to form a volatile complex containing the borates by the addition of additional boron trifluoride to the bottom of the benzene column. The complex is concentrated by fractionation into a benzene recycle stream removed from the benzene column as a sidecut. The benzene recycle stream is then passed through a bed of activated alumina which selectively removes the complex. This is described in greater detail in U.S. Pat. No. 3,238,268. An alternative method in which an olefin-acting compound, such as ethylene or butylene, is passed into the bottom of the benzene column is described in U.S. Pat. No. 3,631,122.

The liquid phase portions of the reaction zones which remain at the reduced pressure of the low pressure separator are passed into a benzene column, which is operated under conditions effective to recover essentially all of the remaining benzene from the combined reaction zone effluent. This column is preferably operated with a bottom pressure of about 15 psig. and with about a 5 psig. pressure drop through the column. The liquid temperature at the bottom of the column will be maintained at about 350° F. to ensure complete removal of the benzene from the alkylated benzene being withdrawn as a bottoms liquid product. The temperature at the top of the column will be about 200° F. under these conditions. As used in this description, references to the benzene column are intended to refer generically to the fractionation column in which unreacted aromatic hydrocarbons are separated as a top product. This aromatic may be toluene, etc., but for convenience is assumed to be benzene.

The bottoms product of the benzene column is preferably passed into a second distillation column which is commonly referred to as an ethylbenzene column when ethylbenzene is being produced. Conditions suitable for operation of the second column include a pressure of about 10 psig. and a bottom temperature of about 425° F. An overhead vapor which is essentially pure ethylbenzene is removed as the net overhead product at a temperature of about 280° F. The design of these last two fractionation columns and their associated equipment, such as fractionation trays, is well within the expertise of those skilled in the art, and they may be of conventional design. The ethylbenzene column is located within the fractionation zone 42. This zone may contain only the ethylbenzene column and produce a bottoms stream of polyalkylated benzenes which are recycled to the transalkylation zone as in U.S. Pat. No. 3,126,421. Alternatively, the bottoms of the ethylbenzene column may be passed into a third fractionation column. Heavy polymers, etc., referred to as tar would be removed as the bottoms stream of this third column, and the polyalkylated benzenes would be removed as an overhead vapor stream. This fractionation system is shown in U.S. Pat. No. 2,995,611.

A net overhead gas stream is removed from the benzene column. This gas stream contains various light hydrocarbons, such as saturate $C_2$ to $C_5$ paraffins, which were dissolved in the liquids fed to the benzene column and also boron trifluoride dissolved in these liquids. It also will contain some boron trifluoride which was passed into the column as previously described to prevent borate deposition. This gas stream must be passed into a promoter recovery zone in which the boron trifluoride is recovered for reuse and to facilitate the discharge of the off-gas from the process. A suitable recovery zone configuration for use with the preferred catalyst system is shown in U.S. Pat. No. 3,126,421. The gas stream is passed upward through an absorption tower having about 12 trays countercurrent to a lean oil, and the boron trifluoride transfers into the lean oil. The resultant rich oil is then stripped to recover the boron trifluoride in a 24-tray stripping column. The lean oil may be polyalkylated benzenes such as are formed in the process. This lean oil preferably contains about 15-20% dimethoxybenzene (DMB). DMB forms a weak, thermally unstable complex on contact with the boron trifluoride and is easily recovered upon heating the lean oil in the stripper. The gases removed from the absorber column are passed through a caustic neutralization media to produce an environmentally acceptable effluent. Other types of equipment or different lean oils or additives may be used to recover other catalyst promoters.

The absorber in the promoter recovery zone is preferably operated at a higher pressure than is desired for use at the top of the benzene column. Therefore, the net off-gas of the benzene column which is to be passed into the promoter recovery zone, as well as that portion to be recycled to the reaction zone as in the prior art, must be compressed to be passed into the absorber. The additional compressor capacity required to do this increases both the capital cost and utility cost of the process. It is an objective of this invention to provide a process for the alkylation of aromatic hydrocarbons wherein a compressor is not necessary to pass the off-gas of the benzene column into a catalyst promoter recovery zone operating at a higher pressure than the benzene column.

According to the inventive concept at least a part of the motive force required to pass the net benzene column overhead gas into the promoter recovery zone is derived by depressurizing the vaporous phase of the alkylation zone effluent stream. This vaporous phase is comprised of the unreactive saturated paraffins contained in the olefin feed stream and boron trifluoride. In comparison, the effluent of the transalkylation zone will normally and preferably contain very little vapor, and therefore preferably is not used in the same manner as the alkylation zone effluent. As previously specified, the alkylation zone effluent preferably has a pressure ranging from about 300-600 psig. The pressure specified for the top of the benzene column was about 5 psig. There is therefore normally available a pressure differential of about 280 to 580 psig. between the low pressure stream to be pumped and the high pressure stream fed to the ejector. The ejector itself may be of customary design and can be chosen by those skilled in the art. Preferably, the outlet of the ejector will be at a pressure above about 50 psig. The relatively high pressure vapor-liquid separator in which the effluent of the alkylation zone is separated into vapor and liquid fractions may also be of customary design and is referred to herein as the high pressure separator or the first vapor-liquid separation zone. At least a portion of the vapor stream removed from this separation zone is used as the high pressure stream fed to the ejector. A second portion may be bypassed as desired to control the operation of the ejector.

The liquid stream removed from the first vapor-liquid separation zone preferably comprises most of the $C_6+$ hydrocarbons in the alkylation zone. It therefore contains the aromatic hydrocarbon and the product alkylaromatic hydrocarbon. It will also contain an equilibrium concentration of lower boiling hydrocarbons, such as ethane, and boron trifluoride and some polyalkylated aromatic hydrocarbons. Preferably, this liquid stream is admixed with the effluent of the transalkylation zone and passed into a second vapor-liquid separation zone. Referring to the Drawing, this zone may be comprised only of the low pressure separator 15 or it may contain both the low pressure separator 15 and a third vapor-liquid separator 20. The second vapor-liquid separation zone is preferably operated at a pressure in the range of about 20-65 psig. Lower pressures may be used, but this pressure range allows the liquids to be transferred into the benzene column without the use of a pump. The pressure in this zone should also be greater than in the promoter recovery zone or its equivalent. Heat may be recovered from the reaction zone effluents through the use of a heat exchanger in line 14.

The vapor phase stream removed from the low pressure separator 15 contains boron trifluoride and low boiling point hydrocarbons which are released from the entering liquid stream due to the lower pressure in the separator. It will also contain the boron trifluoride and light hydrocarbons contained in the effluent of the ejector and an equilibrium concentration of less volatile hydrocarbons such as the aromatic hydrocarbon. It is preferred that this vapor phase stream is cooled, as to about 100° F., and then passed into the third vapor-liquid separator. This has such advantages as allowing the low pressure separator 15 to be operated at a relatively warm temperature which produces a liquid phase effluent stream having a proper temperature for passage into the benzene column. Cooling the vapor phase effluent of the low pressure separator 15 produces a liquid phase containing the aromatic hydrocarbon. This valuable material is therefore not lost to the catalyst promoter recovery zone. The remaining uncondensed vapors are then passed into the promoter recovery zone. These vapors include boron trifluoride and light hydrocarbons removed from the top of the benzene column and which have been recycled without the use of a compressor, thereby achieving an objective of the invention.

In accordance with this description, a broad embodiment of the invention may be characterized as a process for the alkylation of aromatic hydrocarbons which comprises the steps of admixing a catalyst promoter recycle stream, an aromatic hydrocarbon recycle stream and a feed stream comprising an olefinic hydrocarbon to form a reaction zone feed stream; passing the reaction zone feed stream through an alkylation zone maintained at alkylation-promoting conditions and effecting the production of an alkylation zone effluent stream comprising the aromatic hydrocarbon, the catalyst promoter and an alkylaromatic hydrocarbon; passing the alkylation zone effluent stream into a first vapor-liquid separation zone and forming therein a first liquid hydrocarbon stream comprising the aromatic hydrocarbon and the alkylaromatic hydrocarbon and a first vapor stream comprising the catalyst promoter; passing at least a portion of the first vapor stream through an ejector as a motive stream utilized to pump a second vapor stream comprising the catalyst promoter and forming thereby an ejector effluent vapor stream; passing the ejector effluent vapor stream into a second vapor-liquid separation zone; passing the first liquid hydrocarbon stream into the second vapor-liquid separation zone; passing a second liquid hydrocarbon stream comprising the aromatic hydrocarbon and the alkylaromatic hydrocarbon from the second vapor-liquid separation zone to a first fractionation column, and recovering the product alkylaromatic hydrocarbon from a bottoms stream of the first fractionation column; withdrawing from the first fractionation column a net overhead vapor stream comprising the catalyst promoter and passing the net overhead vapor stream into the ejector as the second vapor stream; withdrawing from the second vapor-liquid separation zone a third vapor stream comprising the catalyst promoter, and passing the third vapor stream into a catalyst promoter recovery zone which effects the removal of impurities from the third vapor stream to produce a fourth vapor stream having a higher concentration of the catalyst promoter than the first, the second and the third vapor streams; passing a first portion of the fourth vapor stream into the first fractionation column, and admixing a second portion of the fourth vapor stream as the catalyst promoter recycle stream used to form the reaction zone feed stream; and, withdrawing a fractionation product stream comprising the aromatic hydrocarbon from the first fractionation column, and admixing at least a first portion of the fractionation product stream as the aromatic hydrocarbon recycle stream used to form the reaction zone feed stream.

I claim as my invention:

1. A process for the alkylation of aromatic hydrocarbons which comprises the steps of:
   (a) admixing a catalyst promoter recycle stream, an aromatic hydrocarbon recycle stream and a feed stream comprising an olefinic hydrocarbon to form a reaction zone feed stream;
   (b) passing the reaction zone feed stream through an alkylation zone maintained at alkylation-promoting conditions and effecting the production of an alkylation zone effluent stream comprising the aromatic hydrocarbon, the catalyst promoter and an alkylaromatic hydrocarbon;
   (c) passing the alkylation zone effluent stream into a first vapor-liquid separation zone and forming therein a first liquid hydrocarbon stream comprising the aromatic hydrocarbon and the alkylaromatic hydrocarbon and a first vapor stream comprising the catalyst promoter;
   (d) passing at least a portion of the first vapor stream through an ejector as a motive stream utilized to pump a second vapor stream comprising the catalyst promoter and forming thereby an ejector effluent vapor stream;
   (e) passing the ejector effluent vapor stream into a second vapor-liquid separation zone;
   (f) passing the first liquid hydrocarbon stream into the second vapor-liquid separation zone;
   (g) passing a second liquid hydrocarbon stream comprising the aromatic hydrocarbon and the alkylaromatic hydrocarbon from the second vapor-liquid separation zone to a first fractionation column, and recovering the product alkylaromatic hydrocarbon from a bottoms stream of the first fractionation column;
   (h) withdrawing from the first fractionation column a net overhead vapor stream comprising the catalyst promoter and passing the net overhead vapor stream into the ejector as the second vapor stream;
   (i) withdrawing from the second vapor-liquid separation zone a third vapor stream comprising the catalyst promoter, and passing the third vapor stream into a catalyst promoter recovery zone which effects the removal of impurities from the third vapor stream to produce a fourth vapor stream having a higher concentration of the catalyst promoter than the first, the second and the third vapor streams;
   (j) admixing a first portion of the fourth vapor stream as the catalyst promoter recycle stream of step (a); and,
   (k) withdrawing a fractionation product stream comprising the aromatic hydrocarbon from the first fractionation column, and admixing at least a first portion of the fractionation product stream as the aromatic hydrocarbon recycle stream of step (a).

2. The process of claim 1 wherein a second portion of the fourth vapor stream is passed into the first fractionation column.

3. The process of claim 1 wherein the catalyst promoter is chosen from the group consisting of boron trifluoride, boron trichloride, boron tribromide, hydrogen chloride, carbon tetrachloride, hydrogen fluoride, hydrogen bromide, ammonium fluoride, ammonium chloride, ammonium bromide and ammonium iodide.

4. The process of claim 2 wherein the second vapor-liquid separation zone comprises a first and a second receiving vessel, with the ejector effluent vapor stream being passed into the first receiving vessel; a fifth vapor stream comprising the catalyst promoter is removed from the first receiving vessel, cooled and passed into the second receiving vessel, and the third vapor stream is withdrawn from the second receiving vessel.

5. The process of claim 2 wherein a third portion of the fourth vapor stream is commingled with a second portion of the fractionation product stream and with polyalkylated aromatic hydrocarbons separated from the bottoms stream of the first fractionation column and passed through a transalkylation zone maintained at transalkylation-promoting conditions to form a transalkylation zone effluent stream comprising the aromatic hydrocarbon, the catalyst promoter and the alkylaromatic hydrocarbon, and the transalkylation zone effluent stream is passed into the second vapor-liquid zone.

6. The process of claim 5 wherein the transalkylation zone effluent stream is admixed with the first hydrocarbon liquid stream.

7. The process of claim 6 wherein the aromatic hydrocarbon is benzene and the olefinic hydrocarbon is ethylene.

8. The process of claim 1 wherein the aromatic hydrocarbon is benzene.

* * * * *